United States Patent [19]

Smith

[11] Patent Number: 4,965,209

[45] Date of Patent: Oct. 23, 1990

[54] ISOTOPE ANALYSIS OF CLOSELY ADJACENT MINERALS

[75] Inventor: Michael P. Smith, Tulsa, Okla.

[73] Assignee: Amoco Corporation, Chicago, Ill.

[21] Appl. No.: 338,345

[22] Filed: Apr. 12, 1989

Related U.S. Application Data

[63] Continuation of Ser. No. 88,760, Aug. 24, 1987, abandoned.

[51] Int. Cl.$^5$ ............................................. G01N 33/24
[52] U.S. Cl. ........................................ 436/32; 422/78; 422/80
[58] Field of Search ................................ 436/25–33, 436/43, 44, 46, 57, 59, 127, 139, 144, 145, 155, 182; 422/78, 80

[56] References Cited

PUBLICATIONS

"Mass Spectrometric Determination of Gases in Individual Fluid Inclusions in Natural Minerals", *Anal. Chem.*, Barker et al., vol. 58, No. 7, 6-86, pp. 1330–1333.
"Reviews in Minerology, Fluid Inclusions", vol. 12, *Minerology Society of Amer.*, pp. 109, 117, 122–129.
"Changes in Carbon and Oxygen Isotope Composition During Isotope Diagenesis", Dickson et al., *Sedimentology*, (1980), 27, 107–118.

*Primary Examiner*—Robert A. Wax
*Assistant Examiner*—T. J. Wallen

[57] ABSTRACT

Method and apparatus are provided for analyzing closely adjacent minerals in specimens of naturally occuring minerals. A sectioned mineral sample is mounted on a glass slide and placed in a vacuum chamber. An optical microscope is used to examine the sample through a window in the vacuum chamber. A laser beam is used for pyrolyzing a portion of the specimen causing gases to be released. Gases released from the mineral are analyzed by a mass spectrometer. Relative movement of the sample and laser beam, pyrolysis of target samples, and analysis of released gases can be automated.

18 Claims, 5 Drawing Sheets

ISOTOPE ANALYSIS OF CLOSELY ADJACENT MINERALS

This is a continuation of copending application Ser. No. 07/088,760 filed on Aug. 24, 1987.

1. Field of the Invention

The instant invention relates to methods and apparatus for analyzing carbonates and hydrous minerals such as clays and micas and more particularly to such methods and apparatus in which such minerals are subjected to a laser beam and gases released from the mineral are analyzed.

2. Setting of the Invention

The relative abundance of carbon, hydrogen and oxygen isotopes in natural carbonates, such as limestones, dolomites, and the like and in hydrous minerals, such as clays and micas, can be used to provide information about whether hydrocarbons were present or were likely to be formed during mineral formation and about prevailing temperatures.

The relative abundance of $^{12}C$ isotope relative to $^{13}C$ isotope provides an indication that carbon dioxide of biological origins, also characteristic of hydrocarbons, was present during mineral formation. If the carbonates could be analyzed on a scale of microns, that is, in the range of about 1 to about 1000 microns, then it would also be possible to derive information whether hydrocarbons were present or likely to be formed during periods of mineral developments when migration and accumulation of hydrocarbons was possible.

The greater the relative abundance of $^{1}H$ isotope relative to $^{2}D$ isotope, the greater likelihood that hydrocarbons were present during mineral formation. The relative abundance of $^{1}H$ isotope to $^{2}D$ isotope also provides information about temperature during mineral formation. Information about the isotope ratio can also be used together with information about the $^{16}O/^{18}O$ ratio discussed below to provide information about different waters such as saltwater and freshwater and the like, which were present during mineral formation.

The greater abundance of $^{16}O$ isotope relative to $^{18}O$ isotope provides an indication that elevated temperatures were present during mineral formation. This information can be used as an indication of whether temperature was appropriate for petroleum formation and accumulation. If this information could be obtained on a scale of microns, such as characterizes the cementation layers around mineral grains, then it would be possible to derive information whether conditions were appropriate for hydrocarbon formation during a period of mineral development when migration and accumulation of hydrocarbons was possible.

In the past, simple and economical ways of obtaining information about isotope ratios in minerals on a microscale such as characterizes cementation layers around mineral grains have not been available. One past technique for obtaining information although not on the microscale of interest in this invention, required a selected area of mineral to be drilled and the resulting dust collected and analyzed. Use of drillbits, however, is not feasible on the microscale of interest to the present invention.

This is because the mineral sample to be analyzed may include a plurality of different minerals or cements closely adjacent one another as well as mineral growth formed between and on the various minerals. When such a sample is drilled, gases from different minerals or from one or more cements may be simultaneously released. Such techniques prevent accurate analysis of a particular mineral or cement to obtain information about the environment and age of mineral formation.

There exists a need for a method and apparatus for sampling single minerals or cements in naturally occurring minerals.

There exists a need for such a method and apparatus in which selected minerals and cements from an identified class of minerals and cements may be selectively sampled.

There exists a further need for such a method and apparatus in which a plurality of identified minerals and cements may be individually and sequentially sampled.

SUMMARY OF THE INVENTION

The method of the invention comprises the steps of characterizing a class of minerals or cements formed in a naturally occurring mineral or the like, identifying a target sample of a single mineral or cement within the characterized class; thermally decomposing or pyrolyzing by laser beam the target sample; and analyzing the gases released from the target sample.

According to another aspect of the invention, a second target sample within the characterized class can be identified, thermally decomposed by laser beam, and the resulting released gases analyzed.

In still another aspect of the method, one or more target samples in a single specimen containing a plurality of minerals is identified and thermally decomposed by laser beam and the resulting gases analyzed. Thereafter, one or more target samples in a second mineral in the specimen are thermally decomposed by laser beam and the gases released therefrom analyzed.

According to yet a further aspect of the invention, a mineral sample comprising a plurality of minerals is moved relative to a laser beam, the laser beam is at least periodically caused to thermally pyrolyze portions of the sample, and the resulting gases are collected and analyzed. Thereafter, according to a further feature, the results from the analysis can be correlated to the mineral sample by visual observation of the sample.

In yet another aspect of the invention, apparatus is provided. In a particular aspect, the apparatus comprises a stage for supporting a mineral sample having a plurality of minerals, a laser having a beam for pyrolyzing a portion of the mineral sample causing gases to be released, means for effecting relative movement of the stage and the laser beam effective for causing the beam at successive moments to thermally pyrolyze different portions of mineral sample, and means for collecting and analyzing gases released from the mineral sample by laser pyrolysis.

In accordance with a further aspect of the apparatus of the invention, the means for effecting relative movement can be effective for automatically effecting relative movement in a series of discrete steps, the stage and the laser being immobile relative to one another between each step of the movement and further comprises means for controlling the laser so that the laser beam is caused to thermally pyrolyze a portion of the sample during periods when the stage and the laser are immobile relative to each other.

Additional advantages associated with the instant invention, will become apparent from the following detailed description and the accompanying drawings wherein.

DETAILED DESCRIPTION OF THE PREFERRED EMBODIMENTS OF THE INVENTION

Figure 1:
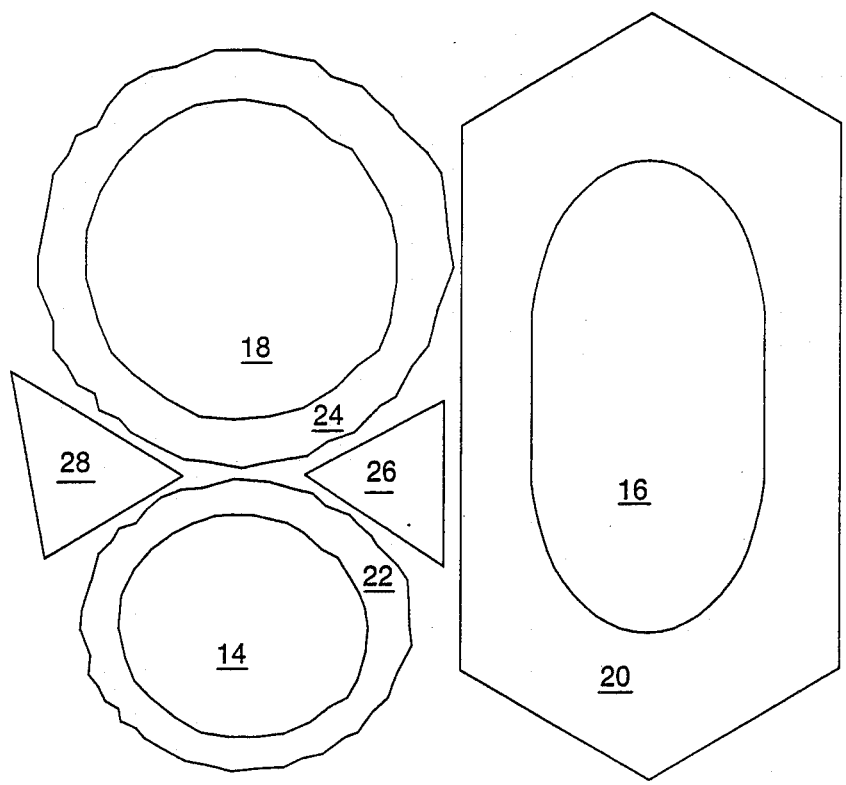
FIG. 1 illustrates a view through a microscope of a portion of sectioned mineral sample specimen containing a plurality of closely adjacent minerals of different origins.

Turning now to the drawings and in particular to FIG. 1, consideration will now be given to a sectioned mineral specimen containing a plurality of closely adjacent mineral growths of different origins. Indicated generally at 10 is a section specimen of naturally occurring mineral. Sample 10 consists of a cut section having a thickness of approximately 0.03—1.0 millimeter which is polished on both sides and which is mounted on a glass slide (not visible in FIG. 1). The view of FIG. 1 is a view of the polished section as seen through a microscope and is, thus, greatly enlarged. The approximate scale can be indicated in that, for example, the various cementation layers are in the range of about 1 to about 100 microns ($\mu$). in diameter. Sample 10 includes a plurality of these mineral growths, like minerals 14, 16, 18, 22, 24, 26, and 28. Minerals 14, 16, and 18 each include a mineral overgrowth 20, 22, and 24, respectively, which acts as and is referred to herein as a cement. Minerals 26 and 28 are interstitial cements.

Mineral specimen 10 thus includes therein a plurality of primary minerals like minerals 14, 16, and 18. These were formed or deposited during an initial stage of mineral formation. Secondary mineral growths 20, 22, 24, 26, and 28 were formed when mineral growth developed in the spaces around and between the primary minerals. It is to be appreciated that the secondary minerals develop at a different time and under different conditions than the primary minerals. There can be more than one stage of secondary mineral formation. Thus, mineral 20 may represent a first stage, minerals 22 and 24 a second stage, and minerals 26 and 28 a third stage of secondary mineral growth. Since formation of these minerals increasingly restricts flow through the mineral being formed, knowledge of whether hydrocarbons were present or likely to be formed at a time when minerals are formed provides information concerning whether formation and migration of hydrocarbons could have occurred.

Sample 10 may be taken from a portion of naturally occurring mineral growth using the usual sawing and polishing techniques. After the sample is cut, polished, and mounted on a slide, the same may be observed through a microscope to obtain the view of FIG. 1. Geologists are able to identify, by observation through microscope, various types of minerals. Such identification is based on well known criteria of shape of mineral growth and various optical properties.

Figure 2:
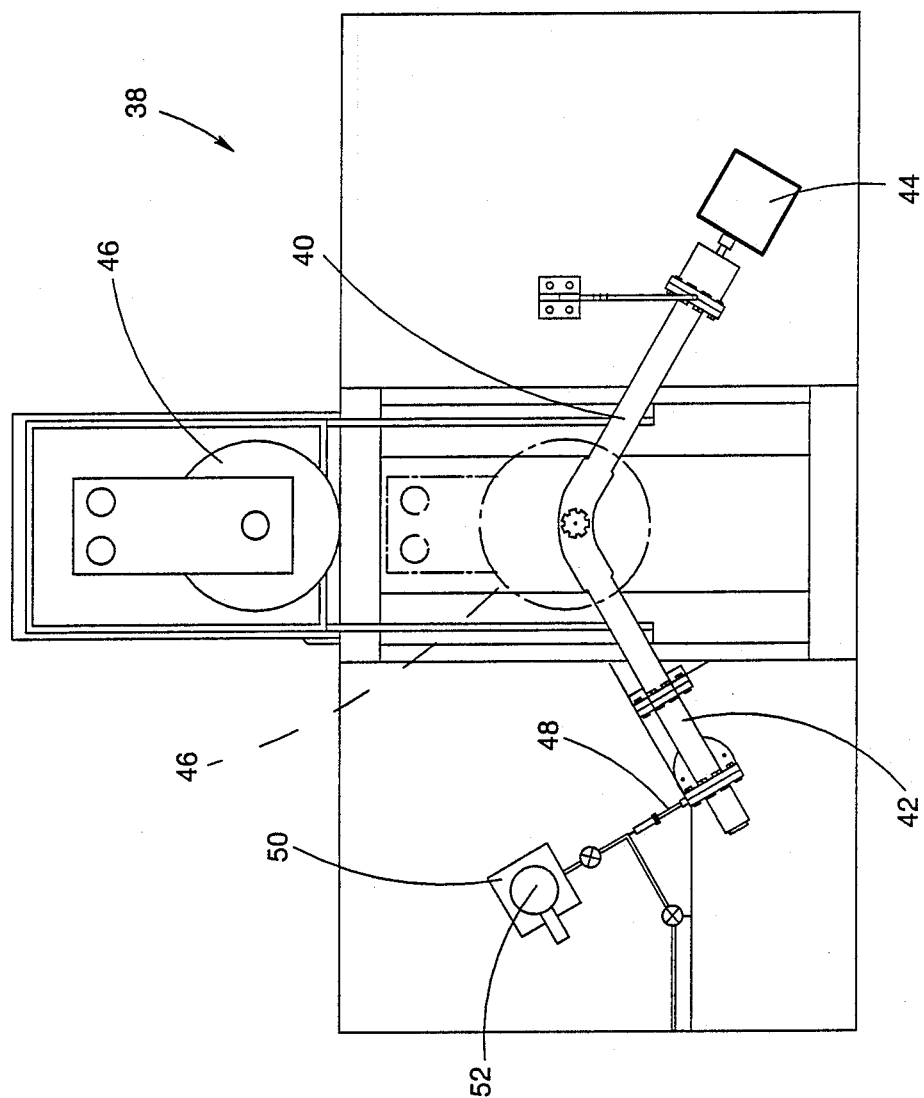
FIG. 2 is a top plan view of apparatus constructed in accordance with the instant invention.
Figure 3:
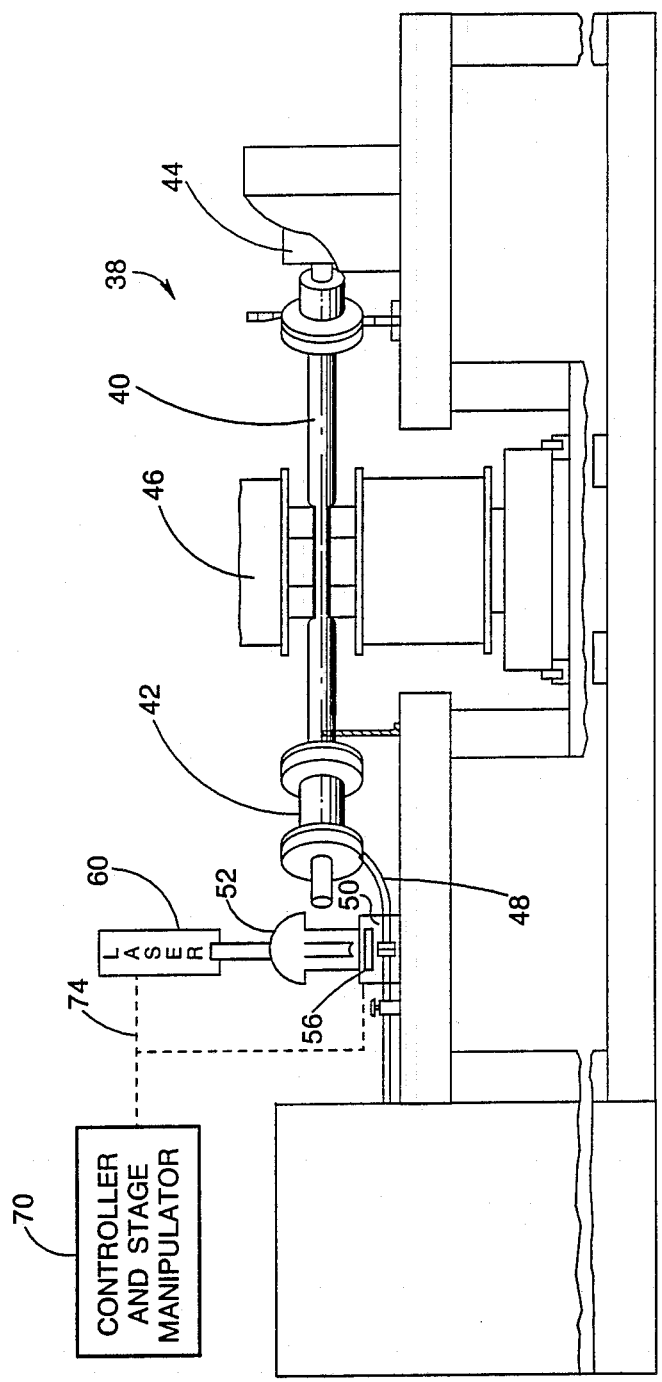
FIG. 3 is a front view of the apparatus shown in FIG. 2.

Turning now to FIGS. 2 and 3, indicated generally at 38 is apparatus constructed in accordance with the instant invention. Included, therein, is a mass spectrometer having a tube 40 having an ionization chamber 42 mounted on one end thereof, and an ion detector 44 mounted on the other end thereof. A magnet 46 is shown in a solid line position in FIG. 2 removed to the rear of tube 40 and in a dashed line position in FIG. 3 about tube 40. A tube 48 is in communication with ionization chamber 42 and provides a gas sample to the ionization chamber 42 for analysis from vacuum chamber 50 of microscope 52 having a laser 74 associated therewith to direct thermally pyrolyzing excitation onto a slide on stage 56 within the chamber 50. In operative condition, a vacuum pump (not shown) maintains a substantial vacuum in tube 40. Controller 70, which can be a commercially available controller, controls movement of stage 56. Preferably the controller 70 can also be used to control laser 74. According to an aspect of the invention, movement of the stage 56 and control of laser beam 73 (See FIG. 4) is coordinated so that thermally pyrolyzing laser excitation is directed onto the sample during periods when movement of the stage is not occurring. The controller can be controlled for moving the stage 56 in discrete steps so that the laser 74 beam can sequentially and successively pyrolyze different samples from the mineral 10.

Stage manipulators drivable in incremental fashion, for example, by stepper motors can be acquired commercially as off-the-shelf items or as custom manufacture. Lasers having computer-controlled shutters and/or microscopes with computer-controlled shutters are similarly commercially available and can be used in the practice of the invention. In accordance with the invention, the movement of a stage and laser pyrolysis are coordinated as described herein. Coordination of control of the stage and the laser can readily be effected by persons skilled in the art from the principles herein described using, for example, a computer or microprocessor for a controller.

That portion of the apparatus, shown in FIGS. 2 and 3 which has been described above, comprises a commercially available gas mass spectrometer, such being also referred to herein as means for analyzing gases. Generally speaking, the gas mass spectrometer operates as follows:

A gas sample to be analyzed is provided to ionization chamber 42 via tube 48. In the ionization chamber, an electron beam ionizes the gases which are then accelerated by an electric field along tube 40 toward magnet 46. The magnetic field alters the direction of travel of the ions in tube 40 depending upon the electrical charge and mass of each ion and upon the strength of the magnetic field. Ions of a certain mass-to-charge ratio travel around the bend in tube 40 toward detector 44. Other ions strike the walls of tube 40 and are not ultimately detected. The foregoing description of the operation of the mass spectrometer describes, in general, the operation of commercially available mass spectrometers. Such mass spectrometers may be used to analyze gases present and to analyze isotope ratios of elements in the gases.

Vacuum chamber 50 is in fluid communication with ionization chamber 42 via tube 48. A commercially available microscope 52 is positioned over vacuum chamber 50. For a more detailed view of vacuum chamber 50, attention is directed to FIG. 4.

Chamber 50 is in fluid communication with ionization chamber 42 (See FIG. 2) via tube 48. As mentioned, tube 40 of the mass spectrometer is maintained in a substantial vacuum by a pump (not shown) and thus tube 48 and chamber 50 are also are maintained in a vacuum.

Figure 4:
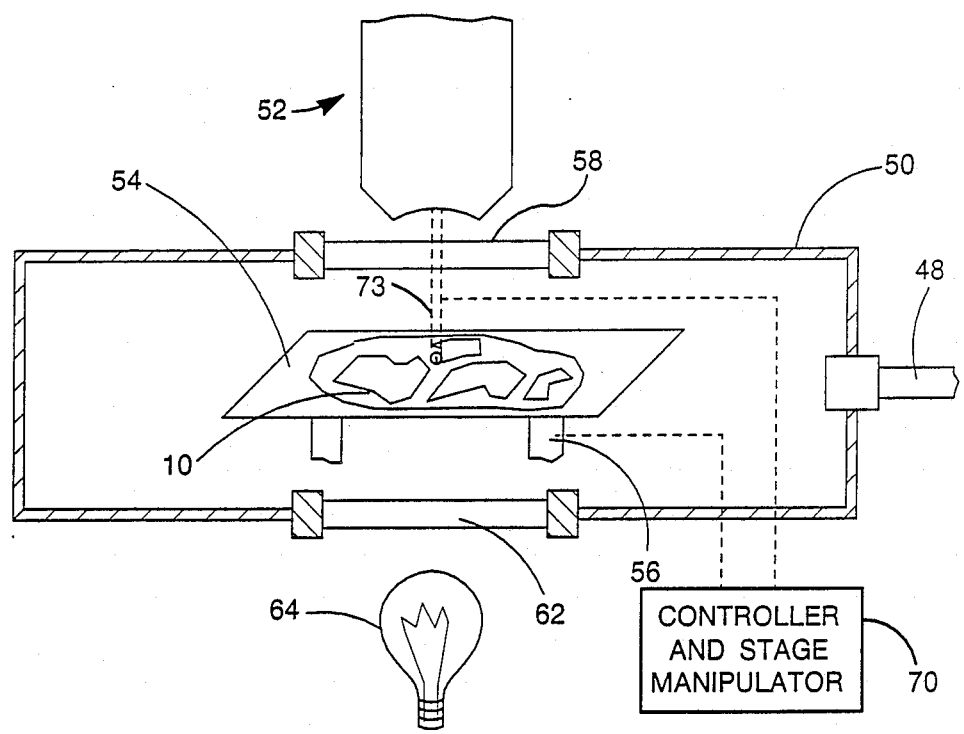
FIG. 4 is an enlarged somewhat schematic view, shown partly in cross-section, of a portion of the apparatus shown in FIGS. 2 and 3.

Sample 10, as will be recalled, is mounted on a glass slide 54, which is viewable in FIG. 4. Slide 54, in the view of FIG. 4, is tilted forward to show sample 10. In operative condition, the slide is substantially parallel to the upper and lower walls of chamber 50. Slide 54 is removably mounted on a commercially available manipulator 56 which enables the slide to be moved laterally and vertically responsive to a commercially available operator control (see discussion of FIG. 3 above) for the manipulator. Chamber 50 includes a glass window 58 formed in an upper wall thereof over which is positioned a lower wall of vacuum chamber 50 beneath window 58. A light 64 is positioned beneath window 62.

Indicated generally at 73 is a laser beam which is directed through the microscope onto a selected specimen of minerals of sample 10.

Figure 5:
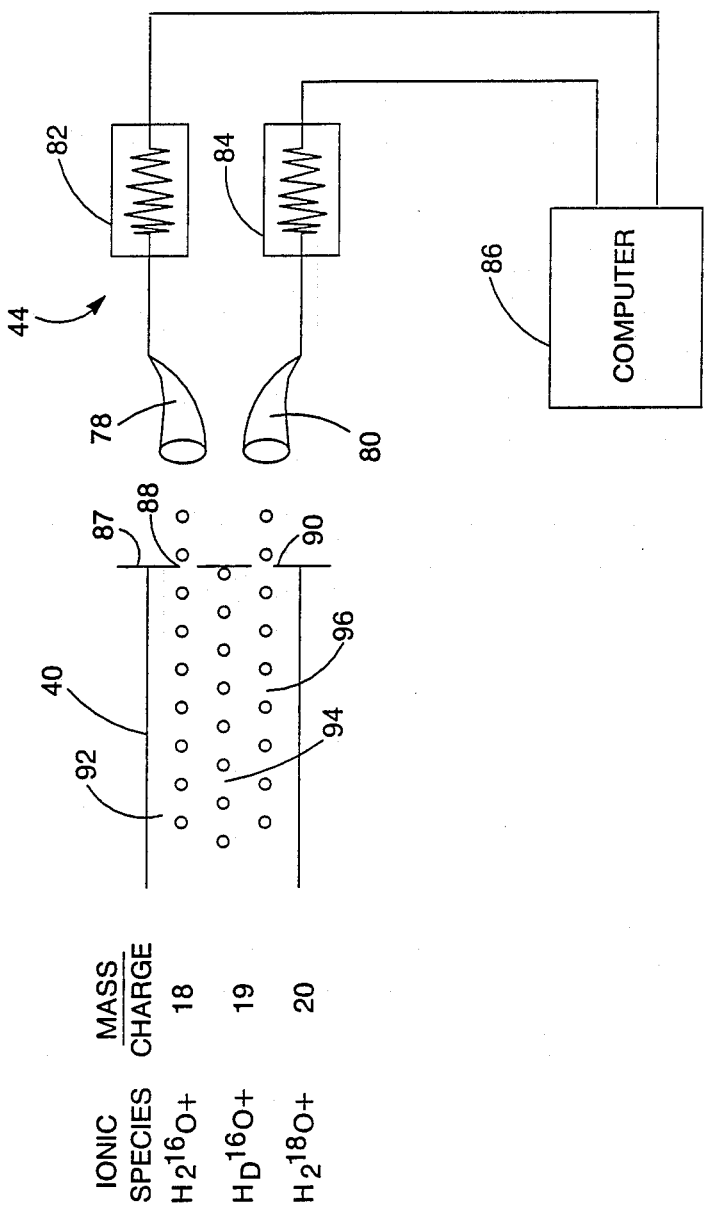
FIG. 5 is a schematic diagram of a portion of the apparatus of FIGS. 2 and 3.

Turning now to FIG. 5, ion detector 44 includes therein a pair of commercially available Galileo-type electron multipliers 78 and 80. Each of the electron multipliers is connected to an associated ion counter 82 and 84 which, in turn, are connected to a commercially available computer 86. The end of tube 40, which is directed toward ion detector 44, includes an end plate 87 having slits, such as slits 88 and 90 formed therein. End plate 87 may be fixed in selected positions relative to tube 40 thereby varying the radial position of the slits relative to the longitudinal axis of tube 40.

Consideration will now be given to the operation of the instant embodiments of the invention. When a mineral growth of interest is located, sample 10 is prepared in the usual fashion. A slice is taken from the mineral growth and is thereafter polished and mounted on glass slide 54, as shown in FIGS. 4 and 5. Thereafter, slide 54 is mounted on manipulator 56 and light 64 is turned on. An operator examines sample 10 through microscope 52 and positions the same between the microscope lens using the controller 70 for manipulator 56. The operator searches for a class of minerals of interest, for example, the class of minerals illustrated by 26, 28 in FIG. 1. Next a single mineral specimen of interest is identified under the microscope. Then, a low intensity beam can be used to specifically position the laser beam for later sampling. Then, a higher intensity laser beam sufficient to pyrolyze minerals on the surface of the specimen can be used to pyrolyze and generate gases which can be analyzed in the analysis. Only a relatively small amount of energy is required for pyrolysis of a portion of the target sample, for example, about 500 microwatts will suffice. Manipulator 56 may also be moved in order to position the slide relative to beam 73. Alternatively, or subsequently, the controller 70 can be controlled for moving stage 56 in stepwise increments beneath the laser beam of laser 70 and the laser can be controlled for directing thermally pyrolyzing radiation onto the sample during periods when the sample is not in motion.

When selected minerals specimens are contacted with laser excitation, at sufficient temperatures, gases are released from the mineral specimen and pass through tube 48 to ionization chamber 42 where the same are ionized. The ionized gases are accelerated in tube 40 toward magnet 46 which changes the direction of travel of the ionized gases.

Often, the minerals of interest in connection with exploration and production of oil and gas are carbonates and hydrous minerals. In the hydrous minerals, the isotope ratios of most interest, and those which have the best chance of being analyzed, are $^{16}O/^{18}O$ $^{1}H/^{2}H$. These ratios can be determined by detecting the following ionic species: $H_2^{16}O+$, $HD^{16}O+$, and $H_2^{18}O+$.

The mass spectrometer is adjusted, by adjusting the power of magnet 46, so that ionic species having a mass to charge ratio of 18, 19, and 20, namely, $H_2^{16}O+$, $HD^{16}O+$, and $H_2^{18}O+$, strike end plate 87.

In FIG. 5, a first ion stream 92 is made up of $H_2^{16}O+$ ions; a second stream 94 is made up of $HD^{16}O+$ ions, and a third ion stream 96 is made up $H_2^{18}O+$ ions. Because each ion stream is made up of ions having a different mass-to-charge ratio, the effect of magnet 46 on the ions is to separate them into very slightly nonparallel streams of ions, each of which strikes end plate 87 in a predetermined location. It can, thus, be seen that by selectively positioning end plate 87 and electron multiplier 78 and 80, an ion stream made up of ions having a selected mass-to-charge ratio may be directed into one of the electron multipliers, while the other ions are absorbed in end plate 87. Each ion in, for example, ion stream 92, which passes through slit 88 and strikes electron multiplier 78 generates a shower of secondary electrons in multiplier 78 which is provided to ion counter 82. Each electron shower is counted by counter 82 as a single ionization event which is recorded by computer 86.

Detector 44 is advantageous when dealing with a very small gas sample, such as that which is released from a single target. Since electron multipliers do not necessarily release the same number of electrons in response to ions having the same mass-to-charge ratio, use of the ion counters to convert each electron shower into a single ionization event increases the accuracy of the collected data. it can be seen that by shifting end plate 87 and electron multiplier 78 and 80, different selected ion streams may be detected. Furthermore, by changing the strength of the magnetic field generated by magnet 46, streams of ions having different mass-to-charge ratios than those shown in the example may be made to strike end plate 87 and/or pass through the slits therein.

In carbonates, the isotope ratios of most interest, and those that have the best chance of being analyzed and are $^{16}O/^{18}O$ and $^{12}C/^{13}C$. These ratios can be determined by detecting the following ionic species:

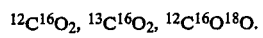

$$^{12}C^{16}O_2, \,^{13}C^{16}O_2, \,^{12}C^{16}O^{18}O.$$

To analyze these compounds, the mass spectrometer is adjusted, by adjusting the power of magnet 46, so that ionic species having a mass to charge ratio of 44, 45, and 46, namely, $^{12}C^{16}O_2$, $^{13}C^{16}O_2$, and $^{12}C^{16}O^{18}O$ strike end plate 87 and/or pass through the slits therein.

It can, thus, be seen that the instant invention permits characterizing a class of minerals and cements such as primary or secondary minerals or cements, by observation (in the instant embodiment of the invention with an optical microscope) and thereafter identifying a single mineral specimen within the characterized class. The identified mineral specimen may then be thermally decomposed and the gases released therefrom analyzed to derive information concerning the prevailing environment when the mineral was formed. Alternatively, the stage 56 carrying sample 10 can be moved beneath the beam of the laser and the thermally pyrolyzing radiation thereby directed onto the surface, so that sequentially and successively a series of gas samples are obtained which can later be correlated with mineral sample 10 by visual observation.

The instant invention may be used to verify whether or not techniques for analyzing gases from specific mineral types are in fact sequentially and individually releasing gas from specifically those minerals. By using the automatic scanning feature of the invention and correlating samples with mineral types viewed under the microscope and sorting the results of analysis by mineral type, data from a particular characterized class of minerals may be readily generated. Generating such data was not possible with the prior art techniques.

It is to be appreciated that additions and modifications may be made to the embodiments of the invention disclosed herein without departing from the spirit of the same which is defined in the following claims.

What is claimed is:

1. A method of determining an indicator of at least one of hydrocarbon formation, migration, and accumulation during mineral development, comprising the steps of:
   searching for a class of minerals in a mineral specimen comprising more than one class of minerals;
   identifying in the mineral specimen a target sample of the thus searched for class;
   directing thermally pyrolyzing laser beam radiation onto surface mineral substance of the target sample in the mineral specimen releasing surface mineral substance pyrolysate gases therefrom; and
   determining isotope composition essentially of the surface mineral substance from analyzing the pyrolysate gases released from the thus pyrolyzed target sample, the isotope composition including isotope(s) selected from the group consisting of carbon, hydrogen, and oxygen isotopes;
   determining an indicator of at least one of hydrocarbon formation, migration, and accumulation during mineral development of the target mineral from thus determined isotope composition of surface mineral substance pyrolysate.

2. The method of claim 1, wherein said method further includes the steps of:
   identifying a second target sample within said searched for class;
   directing thermally pyrolyzing laser beam radiation onto surface mineral substance of the second target sample releasing surface mineral substance pyrolysate gases therefrom;
   determining isotope composition essentially of the surface mineral substance of the second target sample from analyzing the pyrolysate gases released from the second target sample; and
   determining an indicator of at least one of hydrocarbon formation, migration, and accumulation during mineral development of the second target mineral from thus determined isotope composition of surface mineral substance pyrolysate of the second target sample.

3. The method of claim 2, wherein a cement overgrowth is formed on portions of said mineral and wherein said method further comprises the steps of:
   identifying a further target sample formed in the cement overgrowth;
   directing thermally pyrolyzing laser beam radiation onto surface mineral substance of the further target sample; and
   determining isotope composition essentially of the surface mineral substance of the further target sample, from analyzing the pyrolysate gases released from the further target sample; and
   determining an indicator of at least one of hydrocarbon formation, migration, and accumulation during mineral development of the further target mineral from thus determined isotope composition of surface mineral substance pyrolysate of the further target sample.

4. The method of claim 3, wherein a second cement overgrowth is formed on a portion of said mineral and wherein said method further comprises the steps of:
   identifying yet a further target sample in said second cement overgrowth;
   directing thermally pyrolyzing laser beam radiation onto surface mineral substance of the yet further target sample; and
   determining isotope composition essentially of the surface mineral substance of the yet further target sample from analyzing the pyrolysate gases released from the yet further target sample; and
   determining an indicator of at least one of hydrocarbon formation, migration, and accumulation during mineral development of the yet further target mineral from thus determined isotope composition of surface mineral substance pyrolysate of the yet further target sample.

5. The method of claim 2, wherein said class of mineral comprises only primary mineral components.

6. The method of claim 5, wherein said class of minerals comprises only a selected class of primary mineral components.

7. The method of claim 2, wherein said class of minerals comprises secondary mineral components.

8. The method of claim 7, wherein said class of minerals comprises only a selected class of secondary mineral components.

9. The method of claim 1, wherein said method further comprises the steps of:
   searching for a second class of minerals which is formed in such mineral specimen;
   identifying in the mineral specimen a target sample of said second searched for class;
   directing thermally pyrolyzing laser beam radiation onto surface mineral substance of the thus identified target sample of the second searched for class releasing surface mineral substance pyrolysate gases therefrom;
   determining isotope composition essentially of the surface mineral substance of the target sample of the second searched for class from analyzing the pyrolysate gases; and
   determining an indicator of at least one of hydrocarbon formation, migration, and accumulation during mineral development of the target sample of the second searched for class from thus determined isotope composition of surface mineral substance pyrolysate of the target sample of the second searched for class.

10. The method of claim 9, wherein said method further comprises the steps of:
    identifying a plurality of mineral specimens within each of the searched for classes;
    individually and sequentially directing thermally pyrolyzing laser beam radiation onto surface mineral substance of each of the mineral specimens releasing pyrolysate gases form each; and
    determining isotope composition essentially of the surface mineral substance of each of the mineral specimens from analyzing the pyrolysate gases released from each of the mineral specimens; and determining an indicator of at least one of hydrocarbon formation, migration, and accumulation during mineral development of each of the mineral specimens from respective determined isotope compositions of surface mineral substance pyrolysate of each of the mineral specimens.

11. The method of claim 10, wherein the step of individually and sequentially pyrolyzing each of the mineral specimens comprises the steps of:

individually and sequentially pyrolyzing each of such minerals specimens in said first characterized class; and thereafter, individually and sequentially pyrolyzing each of such identified mineral specimens in said second characterized class.

12. A method for analysis of closely adjacent mineral components in a mineral specimen comprising:

sequentially and successively pyrolyzing the closely adjacent mineral components by automatically effecting relative movement of a stage supporting a mineral specimen and a laser having a beam directed for pyrolyzing a portion of surface mineral substance of the mineral specimen;

causing pyrolysate gases to be sequentially released form the closely adjacent mineral components as specimen and laser beam move relative to one another;

periodically collecting pyrolysate gases thus released as the laser beam and the mineral sample move relative to one another;

determining isotope composition essentially of the surface mineral substance of the closely adjacent minerals from analyzing the resulting pyrolysate gases the isotope composition including isotope(s) selected form the group consisting of carbon, hydrogen, and oxygen isotopes; and correlating the results of such analysis with mineral classes int he mineral specimen by correlating visual observation of scar(s) left by the laser beam on the specimen with the thus determined surface mineral substance isotope compositions.

13. Apparatus comprising:

a stage for supporting a mineral specimen comprising more than one class of minerals;

a laser having a beam for thermally pyrolyzing a portion of surface mineral substance of the mineral specimen causing pyrolysate gases to be released;

means for automatically effecting relative movement of the stage and the laser effective for causing the beam at successive times to thermally pyrolyze different portions of the surface mineral substance of the mineral specimen; and means for periodically collecting released pyrolysate gases; and means for determining isotope composition essentially of the surface mineral substance form various portions of the mineral specimen from periodically analyzing gases sequentially released from different portions of the surface mineral substance of the mineral specimen by the laser beam, the isotope composition including isotope(s) selected from the group consisting of carbon, hydrogen, and oxygen isotopes.

14. The apparatus of claim 13 wherein:

the means for effecting relative movement automatically effects relative movement f the stage and the laser beam in a series of discrete steps, the stage and the laser beam being immobile relative to each other between each step of movement, and further comprising:

means for controlling the laser so that the laser beam is caused to thermally pyrolyze portions of the surface of the specimen only during periods when the stage and the laser are immobile relative to each other.

15. The method of claim 1 wherein:

the mineral specimen contains a plurality of closely adjacent minerals of different origins.

16. The method of claim 15 wherein:

the minerals are in the range of about 1 to about 1000 microns in width and comprise cementation layers in the range of about 1 to about 100 microns in width.

17. The method of claim 12 wherein:

the mineral specimen contains a plurality of closely adjacent minerals of different origins.

18. The method of claim 17 wherein:

the minerals are in the range of about 1 to about 1000 microns in diameter and comprise cementation layers in the range of about 1 to about 100 microns in thickness.

* * * * *